United States Patent [19]

Bernhardt et al.

[11] Patent Number: 5,235,051

[45] Date of Patent: Aug. 10, 1993

[54] PYRIDINIUM SALTS CONTAINING ALKOXYSILYL GROUPS

[75] Inventors: Günther Bernhardt, St. Augustin; Margret Haas, Cologne; Heinz Kragl; Gerald L. Larson, both of Troisdorf, all of Fed. Rep. of Germany

[73] Assignee: Hüls Aktiengesellschaft, Marl, Fed. Rep. of Germany

[21] Appl. No.: 777,150

[22] Filed: Oct. 16, 1991

[30] Foreign Application Priority Data

Oct. 31, 1990 [DE] Fed. Rep. of Germany ....... 4034613

[51] Int. Cl.$^5$ ............................. C07F 7/10; C07F 7/16
[52] U.S. Cl. ......................................... 544/69; 546/14
[58] Field of Search ............................ 546/14; 544/69

[56] References Cited

U.S. PATENT DOCUMENTS 3,700,844 10/1972 Domba ............................. 252/363.5
4,418,195 11/1983 Quinlan ............................. 544/58.2

Primary Examiner—Alan L. Rotman
Attorney, Agent, or Firm—Felfe & Lynch

[57] ABSTRACT

Pyridinium salts of the formula

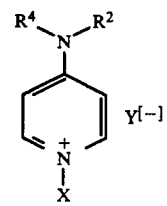

are prepared. The compounds are useful as phase transfer catalysts for the preparation of methacryloyloxyalkylalkoxysilanes and acryloyloxyalkylalkoxysilanes.

1 Claim, No Drawings

PYRIDINIUM SALTS CONTAINING ALKOXYSILYL GROUPS

FIELD OF THE INVENTION

This invention relates to novel pyridinium salts containing alkoxysilyl groups, to a method for their preparation and to their use as phase transfer catalysts.

BACKGROUND OF THE INVENTION

Japanese Patent Application 51348/65 discloses the preparation of methacryloyloxyalkylalkoxysilanes and acryloyloxyalkylalkoxysilanes from alkali metal methacrylates or acrylates and chloroalkylalkoxysilanes, using quaternary ammonium salts as solid/liquid phase transfer catalysts. The reaction temperatures given in this publication are 140° to 180° C. However, according to C. M. Starks and C. Liotta (Phase Transfer Catalysis, Academic Press, New York 1978, page 64), ammonium salts rapidly lose their activity above 110° to 120° C. This explains the low yields of the process described in the Japanese Application. As a result of the thermal decomposition of the quaternary ammonium salts in the presence of alkali metal methacrylates or acrylates, tertiary amines and alkyl methacrylates or acrylates are formed as by-products and, because of similar boiling points, are difficult to separate from methacryloyloxyalkylalkoxysilanes or acryloyloxyalkylalkoxysilanes by distillation.

Methacryloyloxyalkylalkoxysilanes and acryloyloxyalkylalkoxysilanes are frequently used as adhesion promoters in sizes for glass fibers and also as industrially interesting comonomers for the production of sealing compounds and moisture-curable coating systems, for example. However, it is well known by those skilled in the art that high purity is required for industrial use of these methacryloyloxyalkylalkoxysilanes or acryloyloxyalkylalkoxysilanes, for example in sizes for glass fibers or in polymerization reactions.

OBJECTS OF THE INVENTION

It is an object of the present invention to provide phase transfer catalysts for the preparation of methacryloyloxyalkylalkoxysilanes and acryloylalkylalkoxysilanes, which have greater thermal stability than the known quaternary ammonium salts and also produce high yields of silanes of high purity without the necessity of applying expensive purification treatments.

Other objects and advantages of the present invention will become apparent as the description thereof proceeds.

For the sake of simplicity, the methacryloyloxyalkoxysilanes and acryloylalkylalkoxysilanes are hereinafter collectively also referred to as acryloylsilanes.

DESCRIPTION OF THE INVENTION

We have discovered that the above object is achieved with novel pyridinium salts containing alkoxysilyl groups of the formula

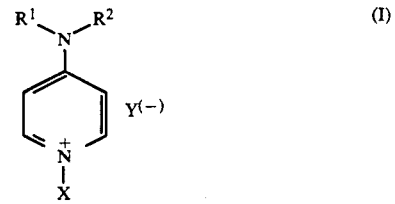

wherein
Y is halogen,
$R^1$ and $R^2$, which may be identical to or different from each other, are each individually aliphatic radicals of 1 to 12 carbon atoms, cycloaliphatic radicals of 5 to 7 carbon atoms, benzyl, or together with each other $(-CH_2-)_p$, where p is 4, 5, or 6, and the ring may be interrupted by an oxygen atom between vicinal carbon atoms, and
X is an organosilane radical of the formula

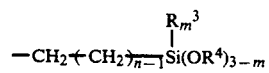

wherein
$R^3$ is alkyl of 1 to 4 carbon atoms,
$R^4$ is alkyl of 1 to 4 carbon atoms or alkoxyalkyl of a total of 2 to 4 carbon atoms,
m is 0, 1 or 2, and
n is 1, 3 or 4.

The novel pyridinium salts of the formula I above may be prepared by reacting an N, N-disubstituted 4-aminopyridine of the formula

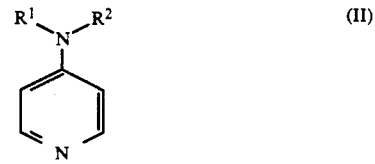

wherein
$R^1$ and $R^2$ have the meanings previously defined, with an haloalkylsilane of the formula

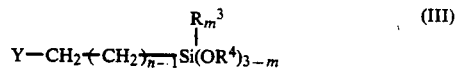

wherein
Y is chlorine or bromine, and
$R^3$, $R^4$, and an n have the meanings previously defined.

Examples of N, N-disubstituted 4-aminopyridine starting compounds for the preparation of the pyridinium salts of the present invention are the following:
4-dimethylaminopyridine,
4-diethylaminopyridine
4-di-n-butylaminopyridine,
4-di-n-hexylaminopyridine,
4-(4'-methylpiperidinyl)-pyridine,
4-morpholinylpyridine,
4-dicyclohexylaminopyridine,
4-dibenzylaminopyridine or
4-piperidinylpyridine.

Examples of haloalkylsilanes of the formula III which are reacted with N,N-disubstituted pyridines of the formula II to give the pyridinium salts of the present invention are the following:
3-chloropropyltrimethoxysilane,
3-chloropropyltriethoxysilane,
chloromethyltrimethoxysilane,
4-chlorobutyltrimethoxysilane,
4-chlorobutyltriethoxysilane,
3-chloropropylmethyldimethoxysilane,
3-chloropropyldimethylmethoxysilane,
3-chloropropylethyldimethoxysilane,
chloromethyldimethylmethoxysilane,
3-chloropropyltris-(methoxyethoxy)-silane or
4-chlorobutyltris-(methoxyethoxy)-silane.

The preparation of the novel pyridinium salts of the present invention is carried out by reacting an N,N-disubstituted 4-aminopyridine with an haloalkylsilane in the absence or presence of a solvent. The molar ratio of 4-aminopyridine to haloalkylsilane may be 1:1 to 1:100. Excess haloalkylsilane is advantageously used as the solvent. Other suitable solvents include toluene, xylene, dimethylformamide, petroleum ether, methanol, ethanol or chlorobenzene.

The reaction temperature for the preparation of the pyridinium salts is 80° to 180° C., preferably 100° to 140° C. At the conclusion of the reaction the pyridinium salts may be isolated by filtration or by distilling off the solvent.

The novel pyridinium salts of the present invention are useful as phase transfer catalysts as such or also together with the solvent in which they are prepared.

The following examples illustrate the present invention and will enable others skilled in the art to understand it more completely. It should be understood, however, that the invention is not limited solely to the particular examples given below.

EXAMPLE 1

1-(3'-trimethoxysilylpropyl)-4-dimethylaminopyridinium chloride 6.1 g (0.05 mol) of 4-dimethylaminopyridine were dissolved together with 9.9 g (0.05 mol) of 3-chloropropyltrimethoxysilane in 50 g of dry o-xylene, and the mixture was heated at the boiling point for 15 minutes. Two phases were formed, of which the lower one solidified in crystalline form upon cooling. The crystals were hygroscopic and were separated by suction filtration in the absence of moisture, and after washing with o-xylene at 70° C. and with n-hexane at 50° C., they were dried in vacuo. The yield was 14.4 g, corresponding to 90.2% of theory. The pyridinium salt had a melting point of 140° to 142° C. The chloride ion determination according to Volhard gave 10.99% chlorine (calculated: 11.05%).

Elemental analysis:
Nitrogen: found 8.6%, calculated 8.7%;
Silicon: found 8.9%, calculated 8.8%.

EXAMPLE 2

1-(3'-triethoxysilylpropyl)-4-(4'-methylpiperidinyl)-pyridinium chloride.

Analogous to Example 1, 5.3 g (0.03 mol) of 4-(4'-methylpiperidinyl)-pyridine were reacted with 7.2 g (0.03 mol) of 3-chloropropyltriethoxysilane.

Yield of pyridinium salt: 11.4 g, corresponding to a yield of 91.3% of theory.

Chloride content: found 8.49%, calculated 8.52%.
Elemental analysis:
Nitrogen: found 6.8% calculated 6.7%;
Silicon: found 6.8% calculated 6.7%.

EXAMPLE 3

(Utility)

1.74 g (0.015 mol) of 4-dimethylaminopyridine were dissolved in 201.5 g (1.015 mol) of 3-chloropropyltrimethoxysilane, and the solution was heated to 135° C. while stirring and maintained at this temperature for 15 minutes. Thereafter, the solution was allowed to cool to 60° C., and 124.2 g (1 mol) of potassium methacrylate and 0.6 g of N,N'-diphenyl-p-phenylenediamine as a stabilizer were added, and the mixture was heated again to 135° C. After one hour, it was cooled, and the potassium chloride which was formed was filtered off and washed with 80 g of methanol. The methanol was evaporated from the combined filtrates, and the residue was distilled under reduced pressure. 228.1 g of 3-methacryloyloxypropyltrimethoxysilane having a boiling point of 83° C. (0.4 mbar) were obtained. The yield was 92% of theory, based on the amount of potassium methacrylate used. The purity was 99.0%. In the gas chromatogram only traces of 4-dimethylaminopyridine were detectable.

EXAMPLE 4

(Comparison to Example 3)

124 g (1 mol) of potassium methacrylate were admixed with 198.5 g (1 mol) of 3-chloropropyltrimethoxysilane, 3.0 g (0.016 mol) of trimethylbenzylammonium chloride and 0.5 g of N,N'-diphenyl-p-phenylenediamine, and the mixture was heated to 135° C. while stirring. After 2 hours at this temperature the mixture was cooled, and the salt component was filtered off and washed with 60 g of methanol. The methanol was evaporated from the combined filtrates, and the residue was distilled under reduced pressure. 195 g of distillate having a boiling point range of 60° to 86° C. (0.3 mbar) were obtained. Gas chromatographic analysis indicated that it contained 35.0 g of 3-methacryloyloxypropyltrimethoxysilane, which corresponds to a yield of 14.1% of theory, based on the amount of potassium methacrylate which was used. The distillate contained 0.37% dimethylbenzylamine and 0.48% benzyl methacrylate. 28.5 g of 3-methacryloyloxypropyltrimethoxy silane having a boiling point of 90° C. (1 mbar) were obtained by distillation through a packed column (packing material: Raschig rings) under reduced pressure. The purity was 97.1%, as determined by gas chromatographic analysis.

While the present invention has been illustrated with the aid of certain specific embodiments, it will be readily apparent to other skilled in the art that the invention is not limited to this particular embodiments, and that various changes and modifications may be made without departing from the spirit of the invention or the scope of the appended claims.

We claim:

1. A pyridinium salt of the formula

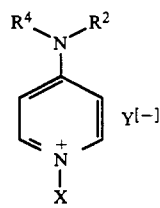

wherein

Y is a halogen,

R¹ and R², which may be identical to or different from each other, are each individually, alkyl or 1 to 12 carbon atoms, cycloalkyl of 5 to 7 carbon atoms or benzyl, or R¹ and R² together with the nitrogen to which they are attached are 4-morpholinyl, 4-piperidinyl or 4-(4'-methylpiperidinyl), and X is an organosilane radical of the formula

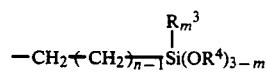

wherein

R³ is alkyl of 1 to 4 carbon atoms,

R⁴ is alkyl of 1 to 4 carbon atoms or alkoxyalkyl of a total of 2 to 4 carbon atoms, m is 0, 1 or 2, and n is 1, 3 or 4.

* * * * *